(12) United States Patent
Stogniew et al.

(10) Patent No.: US 6,753,323 B2
(45) Date of Patent: Jun. 22, 2004

(54) TOPICAL ADMINISTRATION OF AMIFOSTINE AND RELATED COMPOUNDS

(75) Inventors: Martin Stogniew, Blue Bell, PA (US); Jean Bourhis, Sceaux (FR)

(73) Assignee: MedImmune Oncology, Inc., West Conshohocken, PA (US)

( * ) Notice: Subject to any disclaimer, the term of this patent is extended or adjusted under 35 U.S.C. 154(b) by 154 days.

(21) Appl. No.: 09/818,555

(22) Filed: Mar. 28, 2001

(65) Prior Publication Data

US 2003/0022867 A1 Jan. 30, 2003

Related U.S. Application Data

(63) Continuation of application No. 09/298,824, filed on Apr. 26, 1999, now Pat. No. 6,239,119.
(60) Provisional application No. 60/083,071, filed on Apr. 27, 1998.

(51) Int. Cl.$^7$ .......................... A61K 31/66; A61K 31/13
(52) U.S. Cl. ........................................ 514/114; 514/665
(58) Field of Search ................................ 514/131, 740, 514/114, 530, 665

(56) References Cited

U.S. PATENT DOCUMENTS

| 5,488,042 A | 1/1996 | Grdina | 514/114 |
| 5,567,686 A | 10/1996 | Grdina | 514/43 |
| 5,591,731 A | 1/1997 | Kennedy et al. | 514/114 |
| 5,605,931 A | 2/1997 | Hanson | 514/530 |
| 5,869,338 A | 2/1999 | Grdina | 435/375 |
| 5,891,856 A | 4/1999 | Grdina | 514/43 |

FOREIGN PATENT DOCUMENTS

| WO | WO 89/07942 |   | 9/1989 |
| WO | WO96/26643 | * | 2/1994 |
| WO | WO94/03179 | * | 9/1996 |
| WO | WO98/34622 | * | 8/1998 |

OTHER PUBLICATIONS

Tanaka, Tsuneo., An evaluation of the clinical usefulness of Amifostine., The J. of japan society for cancer therapy, 1985, Jun vol. 5, pp. 985–993.*
Buntzel et al., Selective cypoprotection with amifostine . . . , Oto–Rhino–Laryngologia Nove, abstract only, 1997, vol. 7/5–6, pp. 276–280.*
Buntzel et al., The use of amifostine in simultaneous radio–chemotherapy . . . , Zeitschrift fur onkologie, abstract only, 1996, 28/2 pp. 42–49.*
Ben–Josef et al., Radiation Research (1995) 143:107–110.
Bourhis et al., Int. J. Radiat. Oncol. Biol. Phys., (1995) 32:747–752.
Budd et al., Supportive Care Cancer (1994) 2:380–384.
Delaney et al., Int. J. Radiat. Oncol. Biol. Phys., (1995) 32:763–768.
Delaney et al., Cancer (1994) 74:2379–2384.
Geng et al., Int. J. Radiat. Biol., (1992) 61:533–537.
Lowy et al., Radiation Biology (1972) 105:425–428.
Malkinson et al., (1993) J. Inv. Derm. 101(1 Suppl.):135S–137S.
Marks, Cur. Opinion in Oncology (1997) 9:267–273.
Montana et al., Cancer (1992) 69:2826–2830.
Niibe et al., J. Jpn. Soc. Cancer Ther., (1985) 20:984–993.
Niibe et al., Kitakanto Med J.., (1984) 34/5:335–342.
Utley et al., Int. J. Radiat. Oncol. Biol. Phys., (1976) 1, Supp. 1, No. 154.
Verhey et al., Radiation Research (1983) 93, 175–183.

* cited by examiner

Primary Examiner—Vickie Kim
(74) Attorney, Agent, or Firm—Pennie & Edmonds LLP

(57) ABSTRACT

The present invention is directed to methods of treating or protecting mucosal tissue from damage associated with radiation and/or chemotherapeutic treatment of cancers, by the topical application of amifostine and related compounds. These methods avoid the side effects of systemically applied radio/chemo protectants. The invention is also directed to treatment and prevention of infections associated with mucositis by topical application of amifostine and related compounds.

19 Claims, No Drawings

TOPICAL ADMINISTRATION OF AMIFOSTINE AND RELATED COMPOUNDS

This application is a continuation of U.S. patent application Ser. No. 09/298,824, filed Apr. 26, 1999, now U.S. Pat. No. 6,239,119, issued May 29, 2001 which claims priority to U.S. provisional patent application No. 60/083,071, filed Apr. 27, 1998.

1. FIELD OF THE INVENTION

The invention relates to topical use of aminothiols and compositions containing them for the protection from and treatment of radiation and/or chemotherapeutic damage to tissue.

2. INTRODUCTION

The present invention is directed to novel methods of using amifostine and structurally related aminothiols, including aminophosphorothioates, and their metabolites for the topical treatment of tissue. In particular, the invention relates to protecting mucosal, skin or hair tissue from damage by radiation and chemotherapeutic agents, as well as to the treatment of such damaged tissue. In one aspect, the invention encompasses methods of protection of mucosal tissue, and especially mucosal tissue of the head and neck regions, from chemical, radiation, and radio/chemo induced mucositis and conditions related to mucositis, associated with the treatment of cancers. The methods are achieved by the topical application of amifostine, structurally related compounds or their metabolites. The invention also encompasses treatment and prevention of infections associated with mucositis in mucosa of the head and neck region by topical application of amifostine and related compounds. Topical application of these radiochemical protectants allows the use of more aggressive radiochemical treatment schedules while avoiding the toxic effects of systemically administered amifostine.

3. BACKGROUND OF THE INVENTION

3.1 Systemically Administered Amifostine

The compound S-2-(3-aminopropylamino)ethyl dihydrogen phosphorothioate (also known as amifostine, ethiofos, Ethyol®, NSC 296961, and WR-2721, and which will hereinafter be referred to as "amifostine" has been known for over thirty years, and was originally developed by the Walter Reed Institute of Research as an antiradiation agent (radioprotectant) In particular, amifostine was developed for military use against x-ray or nuclear radiation which may be encountered during military conflicts. Bulk amifostine and other aminoalkyl dihydrogen phosphorothioates, and methods to obtain them, are disclosed in U.S. Pat. No. 3,892,824, which is incorporated herein by reference.

In addition to its utility as a military antiradiation agent, amifostine has demonstrated excellent utility as a non-military radioprotectant and chemoprotectant when administered systemically prior to chemotherapy and/or radiation therapy. Amifostine acts to protect normal tissue against the adverse effects which accompany the use of radiochemical therapies for the treatment of various cancers, while largely leaving the target cancerous tissues unprotected. This protective effect is observed in radiation and chemotherapeutic treatments by, for example, alkylating agents such as cyclophosphamide, cisplatin, carboplatin, doxorubicin and its derivatives, and mitomycin and its derivatives. For representative studies, see, e.g., Constine et al., *Int. J. Radia. Oncol. Biol. Phys.*, 12, 1505–1508 (1986); Liu et al., *Cancer*, 69(11), 2820–2825 (1992); Wadler et al., *J. Clin. Oncol.*, 11(8), 1511–1516 (1993); and Buntzel et al., *Ann. Oncol.* 7 (Suppl. 5), 81, 381P (1996).

Similarly, it has been reported that amifostine may be used to protect against the harmful side effects of 3'-azido-3'-deoxythymidine (AZT) therapy. In addition, amifostine and its derivatives appear to exert their protective effects without significantly affecting the beneficial properties of the administered therapeutic agents.

Amifostine is approved in the United States for treatment to reduce the cumulative renal toxicity associated with repeated administration of cisplatin in patients with advanced ovarian or non-small cell lung cancer. *Physicians' Desk Reference*, 51st ed. (1997).

Amifostine is a pro-drug that is dephosphorylated at the tissue site by alkaline phosphatase to the free thiol, which is the active metabolite (WR-1065). Without wishing to be bound by theory, it is believed that once inside the cell, the active free thiol can protect against the toxicities associated with radiation by acting as a scavenger for oxygen free-radicals. (See, Yuhas, in *Radiation-Drug Interactions in Cancer Management*, pp. 303–352 (1977); Yuhas, *J. Natl. Cancer Inst.*, 50, 69–78 (1973); Philips et al., *Cancer Treat. Rep.*, 68, 291–302 (1984)).

Amifostine shows these favorable radioprotective effects when administered systemically prior to radiation treatment. Systemic administration, however, suffers from numerous disadvantages. The typical systemic route of administration is intravenously, but administering compounds intravenously is extremely inconvenient, particularly when a daily dosing schedule for several weeks is necessary. In addition, when amifostine is administered systemically, patients suffer from dose-dependent undesirable side-effects such as nausea, vomiting, emesis and hypotension, as well as flushing or feeling of warmth, chills or feeling of coldness, dizziness, somnolence, hiccups and sneezing. At high enough doses, systemic amifostine is toxic.

3.2 Topically Administered Amifostine

Topical administration of amifostine, if feasible, would be advantageous for a number of reasons. The therapeutic effect of radiation is dose-dependent, so that it would be desirable in many cases to increase the radiation dosage, or use an accelerated radiation schedule, in order to increase the cure rate. Such increased doses of radiation, however, require corresponding increases in amifostine doses in order to counteract the damage to normal tissue accompanying the increased or accelerated radiation schedule. The protective effect of the compound is said to be dependent upon the concentration of amifostine or its active metabolite present in the normal tissue. Because of the adverse side effects of systemic amifostine, however, the amount that can be administered systemically is severely limited. Topical administration would allow greater local control of the amifostine concentration, allowing higher local concentrations without delivery of the higher doses to unaffected tissues and organs. To date, however, topical administration of amifostine has not been shown to be feasible.

The need for an effective topical radiation and chemotherapy ("radio/chemo") protectant is especially acute in patients suffering from radiation or chemically induced damage to mucosal tissue, such as mucositis and conditions associated with mucositis. As a specific example, cancers of the head and neck are often highly localized, and would benefit from aggressive radio/chemo treatment. The normal mucosal tissues of the head and neck region, such as the oral mucosa, are susceptible to chemical and radiation damage. Chemical, radiation, and combined radiation and chemical treatment act to deplete the mucosal basal epithelium, thinning the tissue and causing inflammation, swelling, erythema and ultimately ulceration.

Ulceration of the mucosa leads to additional complications, as the exposed underlying tissue is vulnerable to infection. For example, Bourhis et al. evaluated an accelerated radiation schedule in patients suffering from locally advanced head and neck cancers. Bourhis et al., *Int. J. Radiat. Oncol. Biol. Phys.*, 32(3), 747–752 (1995). In all of the patients treated with the accelerated schedule, confluent mucositis was observed, and more than half of the patients required hospitalization to treat the mucositis. Similar results were reported by Delaney et al. (96% showed confluent mucositis), following a different aggressive radiotherapy schedule. Delaney et al., *Int. J. Radiat. Oncol. Biol. Phys.*, 32(3), 763–768 (1995). But for the sensitivity to head and neck mucosal tissue to radio/chemo damage, more aggressive therapeutic treatments including increased radiation doses and accelerated radiation schedules could be particularly effective at treating cancers in these regions. Thus, protection of mucosal tissue of the head and neck regions would be especially advantageous.

3.2.1 Topical Application to Non-Mucosal Tissue

Although much is known about the radioprotective effects of systemically administered amifostine and related compounds, relatively little is known about the effects of these compounds when administered topically. The few studies which have addressed topical administration have produced inconclusive results.

In an early study, Utley et al. found that topical administration of amifostine in carbowax to the oral mucosa of mice subjected to whole head irradiation prevented oral radiation death syndrome (LD50/8-10) by a factor of 1.4, with no toxicity observed at the dosages tested. Utley et al., *Int. J. Radiat. Oncol. Biol. Phys.*, 1, Supp. 1, No. 154 (1976). Systemically administered amifostine was found to be more effective in preventing oral radiation death, although some deaths due to drug toxicity were reported. The study did not address protection of other tissues or of the oral mucosa per se from mucositis.

Several studies have looked at the radioprotective effects of topical amifostine on radiation-induced damage to non-mucosal tissue, particularly to rat and mouse skin.

In an early pre-clinical study, Lowy et al. studied the radioprotective effects of systemically and topically administered amifostine in mice. Lowy et al., *Radiation Biology*, 105, 425–428 (1972). The amifostine was administered to mouse skin as a paste formed from an aqueous sodium bicarbonate solution (pH 7) and Unibase. Although the study found systemically administered amifostine to be effective in reducing the severity of radiation damage, topically applied amifostine was found to provide no radioprotective effect at any dose studied.

Similarly, Verhey et al. found amifostine to be ineffective to protect mouse skin from radiation-induced damage when applied topically. Verhey et al., *Radiation Research*, 93, 175–183 (1983). A gauze saturated with a 10% solution of amifostine in saline was applied to murine skin for 15 to 60 minutes, followed by $^{137}CS$ irradiation. The study found no significant radioprotective effects for topically-applied amifostine.

More recently, Geng et al. compared the effects of topically and systemically administered 16,16 dm prostaglandin $E_2$ ($PGE_2$) and amifostine on radiation-induced alopecia in mice. Geng et al., *Int. J. Radiat. Biol.*, 61(4), 533–537 (1992); see also Malkinson et al., *J. Invest. Dermatol.*, 101(suppl), 135S–137S (1993), reporting similar results. In the topical studies, a 0.3 mg sample of the dephosphorylated form of amifostine, WR-1065, in 0.2 mL Ringer's solution was administered to the depilated mouse skin prior to fractionated irradiation treatment, then the rate of hair regrowth was studied as a function of radiation dosage. Although topically administered WR-1065 showed some effectiveness in protecting hair matrix cells from radiation-induced injury, the Geng study found systemically administered amifostine to be more effective at all radiation doses studied.

3.2.2 Topical Application to Mucosal Tissue

Several studies have examined the possibility of using amifostine or related compounds topically to protect intestinal mucosal tissue from radiation damage.

Ben-Josef et al. demonstrated that amifostine applied topically by an intrarectal injection of a 2% amifostine gel results in an accumulation of the amifostine metabolite WR-1065 in the rectal wall of rats. Ben-Josef et al., *Radiation Research*, 143, 107–110 (1995). The study did not, however, examine the radioprotective effect in mucosal tissue that might result from the accumulated WR-1065.

Montana et al. tested the effect of amifostine applied topically to protect intestinal mucosa in patients undergoing radiation treatment of the pelvis. *Cancer*, 69(11), 2826–2830 (1992). An amifostine in Proctofoam preparation was administered topically by enema at dosages of 100 to 450 mg per enema 45 minutes prior to pelvic radiation treatment. The Montana et al. study found that topically applied amifostine avoided many of the side effects typically observed when the drug is administered systemically. However, no significant differences were found in rectal mucosal damage between a control group, which did not receive amifostine, and a test group, which received the topical amifostine treatments. Montana et al. speculated that the lack of protective effect may be due to the mode of administering the drug.

An opposite conclusion was reached in an animal study by Delaney et al. Delaney et al., *Cancer*, 74(8), 2379–2384 (1994). Delaney et al. studied the radioprotective effect of topical solutions of amifostine injected into the small intestine of rats. Amifostine was prepared in a pH 9 Tris buffer (tris(hydroxymethyl)aminomethane) at a concentration of 150 mg/mL, and administered intralumenally prior to irradiation of the exteriorized rat small bowel. The study concluded that amifostine, and particularly amifostine in an alkaline vehicle, was an effective radioprotector against intestinal mucositis in rats.

Clearly, the results of these limited studies have been inconclusive and can be considered contradictory. There is some evidence that topical amifostine or WR-1065 may provide protection of skin or intestinal mucosa, but the studies to date show conflicting results. In addition, the studies of mucosal tissues to date have focused on intestinal mucosa and the effects of radiation induced mucosal tissue damage that accompanies pelvic irradiation. Some studies suggest that the vehicle used to deliver the active agent may be a factor to consider in determining potential efficacy.

Mucosal tissues of the head and neck region are particularly sensitive to radiation and chemically-induced damage association with radiochemical treatment of head and neck cancers. Mucositis of these tissues results in extreme patient discomfort, as well as in complications due to infection of ulcerated mucositic tissues. There has yet to be identified a safe and effective method of protecting the mucosal tissues of the head and neck region from radiochemically-induced damage without the undesirable side effects of systemic administration of protectant drugs.

Thus, there is a need for a safe and effective method of protecting tissues from damage due to radio- or chemotherapeutic treatments while avoiding the undesirable effects of systemically administered radio/chemo protectants.

4. SUMMARY OF THE INVENTION

The present invention relates to methods of protecting or treating tissue, skin or hair, particularly mucosal tissue, from damage associated with radiation treatment and chemotherapy, while avoiding the undesirable side effects associated with conventional systemic administration of radio/chemo protectant compounds.

One aspect of the invention relates to protection of tissue by topically administering to the tissue prior to, during, or after, or preferably both prior to and during irradiation and/or chemotherapy, a therapeutically effective amount of an aminophosphorothioate or aminoalkyl thiol compound. The aminophosphorothioate or aminoalkyl thiol compound has the formula:

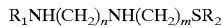

wherein:

R$_1$ is hydrogen, C$_5$–C$_7$ aryl, C$_2$–C$_7$ acyl, or C$_1$–C$_7$ alkyl;

R$_2$ is hydrogen, PO$_3$H$_2$ or R$_3$, wherein R$_3$ is R$_1$NH(CH$_2$)$_n$NH(CH$_2$)$_m$S—; and n and m are each independently an integer from 1 to 10, preferably from 2 to 6.

The invention also encompasses pharmaceutically acceptable salts, solvates and hydrates of the aminophosphorothioate or aminoalkyl thiol compounds.

In another aspect, the invention relates to protection of mucosal tissue by topically administering to the mucosal tissue prior to, during, or after, or preferably both prior to and during irradiation and/or chemotherapy, a therapeutically effective amount of the aminophosphorothioate or aminoalkyl thiol compounds described herein.

It is surprisingly discovered that the aminophosphorothioate or aminoalkyl thiol compounds also exhibit significant antibacterial properties. Thus, another aspect of the invention relates to a method of protecting tissue from bacterial infection, or treating the tissue for infection, by topically administering to the affected tissue the aminophosphorothioate or aminoalkyl thiol compounds described herein. This is particularly advantageous given the secondary infections that can occur in cancer patients, particularly mucosal tissue infections in patients undergoing treatment with radiation and/or chemotherapy.

In a further aspect, the present invention encompasses a method of protection or treatment of tissues from radiation or chemically induced damage and from infection by topically administering to the tissue the aminophosphorothioate or aminoalkyl thiol compounds described herein. Such tissue includes hair, skin and mucosal tissue.

In another aspect, the invention relates to self-preserving multi-dose pharmaceutical preparations which contain an aminophosphorothioate or aminoalkyl thiol compound.

5. BRIEF DESCRIPTION OF THE FIGURES

FIG. 1 shows the weight loss of mice irradiated on the lip with a single dose of 16.5 Gy, in groups which received systemic amifostine, topical amifostine, and a control group which received no amifostine.

FIG. 2 shows the lip mucosal reaction scores for the irradiated mice.

6. DETAILED DESCRIPTION OF THE INVENTION

The present invention provides for methods of treatment of tissue, hair and skin, particularly mucosal tissues, to protect these tissues from radiation and chemically-induced damage without the well-known side effects of systemically administered mucoprotectant compounds. The invention arises, in part, from the surprising discovery that the radioprotectant compound, amifostine, and structurally related compounds and metabolites, can be effectively and safely applied topically to tissues, including mucosal tissues, to provide significant radioprotection. The specific compounds which can be used, their methods of use, and examples of their use are described in the following sections. These include prodrugs, metabolites, derivatives and analogues of amifostine as well as salts, solvates and hydrates of these compounds.

The invention also encompasses an improved therapy for the treatment of neoplastic disorders in humans by utilizing the topical application of the compounds described herein before, during and/or after treatment with radiation or chemotherapeutics. This topical application can both treat and protect the patient from damage including mucositis and related disorders as well as bacterial infection.

6.1. Protection By Topically Applied Amifostine And Related Compounds

In one embodiment, the present invention relates to topical administration of one or more aminoalkyl phosphorothioate or aminoalkyl thiol compounds to tissue, skin or hair, prior to, during and/or after irradiation and/or administration of chemotherapeutic treatments.

6.1.1 Compounds

Compounds which can be advantageously administered according to the methods described herein are aminoalkyl phosphorothioate or aminoalkyl thiol compounds which exhibit selective radioprotection or chemoprotection of normal tissues. Such aminoalkyl phosphorothioate or aminoalkyl thiol compounds, as well as pharmaceutically acceptable salts and/or hydrates thereof, are either known to those of skill in the art or can be identified without undue experimentation using established tests routinely employed in the art.

Compounds that can be used within the present invention include amifostine (WR-2721), as well as salts, hydrates, active metabolites, pro-drugs, and functional derivatives or analogues. More specifically, the invention includes all pro-drugs and metabolites of amifostine and pro-drugs of the active metabolites. Thus, compounds known to the skilled artisan to be suitable for administration to humans and known to be metabolites or otherwise converted into active thiols including metabolites such as WR-1065 and WR-33278 (disulfide), and WR-151327 and its active thiols, including metabolites such as WR-151326 and its corresponding disulfide, are encompassed within the present invention.

Similarly, included herein are aminothiols that exhibit activity similar to that of amifostine or its metabolites. Preferably, these compounds are structurally related to amifostine. Alternatively, these compounds are prodrugs that are metabolized in vivo to a biologically active agent. These compounds are also encompassed by the present invention. Specific examples are illustrated herein.

Aminothiol compounds which can be used in the present invention are represented by the following formula (I):

wherein $R_1$ is hydrogen, $C_5$–$C_7$ aryl, $C_2$–$C_7$ acyl, or $C_1$–$C_7$ alkyl; $R_2$ is hydrogen, $PO_3H_2$ or $R_3$, wherein $R_3$ is $R_1NH(CH_2)_n(CH_mS$—; and n and m are each an integer from 1 to 10, preferably from 2 to 6.

The methods of the present invention also encompasses the use of pharmaceutically acceptable salts and hydrates of the compounds of formula (II) above.

Preferred compounds useful in the methods of the invention are the S-ω(ω-amino-alkylamino)-alkyl dihydrogen phosphorothioate analogues represented by the formula:

R—NH—(C$_n$H$_{2n}$)—NH—(C$_m$H$_{2m}$)—S—PO$_3$H$_2$ wherein R is hydrogen or an alkyl group containing 1 to 7 carbon atoms and m and n independently have a value of from 1 to 10, preferably 2 to 6.

Amifostine (WR-2721) has the structure:

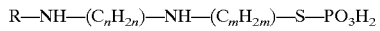

One preferred metabolite of amifostine is a dephosphorylated free thiol form known as WR-1065 (chemical nomenclature: S-2-(3-aminopropylamino) ethanethiol), which can be depicted as follows:

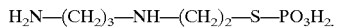

Another preferred metabolite of amifostine is its disulfide, known as WR-33278 ([2-[(aminopropyl)amino]ethanthiol]-N, N'-dithioidi-2,1-ethanediyl)bis-1,3-propanediamine), which can be depicted as follows:

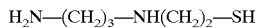

A preferred analogue of amifostine is the compound designated as WR- 151327 (chemical nomenclature: 1-propanethiol-3-[[3-(methylamino)propyl]amino]-dihydrogen phosphothiorate), which can be depicted as follows:

Another preferred analogue of amifostine is the compound designated WR- 151326, a dephosphorylated free thiol form of WR-151327 having the chemical structure:

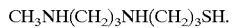

Other specific compounds suitable for use in the present invention include, but are not limited to:
S-1-(aminoethyl)phosphorothioic acid (WR-638);
S-[2-(3-methylaminopropyl)aminoethyl]phosphorothioate acid (WR-3689);
S-2-(4-aminobutylamino)ethyl phosphorothioic acid (WR-2822);
3-[(2-mercaptoethyl)amino]propionamide p-toluene-sulfonate (WR-2529);
S-1-(2-hydroxy-3-amino)propyl phosphorothioic acid (WR-77913);
2-[3-(methylamino)propylamino]ethanethiol (WR-255591);
S-2-(5-aminopentylamino)ethyl phosphorothioic acid (WR-2823);
1-[3-(3-aminopropyl)thiazolidin-2-Y1]-D-gluco-1,2,3,4,5 pentane-pentol dihydrochloride (WR-255709).

Additional aminothiols suitable for use in the present invention include, but are not limited to, S-2-(3-ethylaminopropylamino)ethyl dihydrogen phosphorothioate, S-2-(3-aminopropylamino)-2-methylpropyl dihydrogen phosphorothioate, S-2-(2-aminoethylamino)-2-ethyl dihydrogen phosphorothioate, S-2-(4-aminobutylamino)-2-ethyl dihydrogen phosphorothioate, S-2-(5-aminopentylamino)-2-ethyl dihydrogen phosphorothioate, S-2-(6-aminohexylamino)-2-ethyl dihydrogen phosphorothioate, S-2-(2-methylaminoethylamino)-2ethyl dihydrogen phosphorothioate, S-2-(3-methylaminopropylamino)-2-ethyl dihydrogen phosphorot3-methyamino-propylamino)-3-propyl dihydrogen phosphorothioate (WR-151327) and pharmaceutically acceptable salts thereof. Preferably, the aminothiol is amifostine, WR-1065, WR-33278, WR-151327 or WR-151326; most preferably it is amifostine.

Amifostine, and many of its salts, analogues and derivatives thereof suitable for use in the methods of the invention are commercially available, or can easily be prepared using standard techniques. The aminothiol compounds useful in the methods of the invention may be prepared by methods known in the art (see, e.g., Cortese, 1943, *Organic Synthesis* pp. 91–93, Coll. Vol. II, Blatt, Ed., John Wiley & Sons, Inc., New York, N.Y.; Akerfeldt, 1960, *Acta Chem. Scand.* 14:1980; Piper et al., 1966, *Chem. Ind.* (London):2010). Certain aminothiol compounds, as well as methods of synthesizing such compounds, are described in detail in U.S. Pat. Nos. 3,892,824, 5,424,472 and 5,591,731, and WO 96/25045.

The aminothiol compounds useful in the methods of the invention may be in the form of free acids, free bases, or pharmaceutically acceptable addition salts thereof. Such salts can be prepared by treating an aminothiol compound with an appropriate acid and/or base. Such acids include, by way of example and not limitation, inorganic acids such as hydrohalic acids (hydrochloric, hydrobromic, hydrofluoric, etc.), sulfuric acid, nitric acid, phosphoric acid, etc. and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

The aminothiol compounds useful in the methods of the invention, as well as the pharmaceutically acceptable addition salts thereof, may be in a hydrated, solvated or anhydrous form. Methods of preparing such forms will be apparent to those of skill in the art of organic chemistry.

In another preferred embodiment, the compound is a salt of WR-1065, preferably a succinate, a pamoate, a bis (trifluoroacetate) or a di-hydrochloric acid salt. The solubilities of these salts are shown in the Examples section below.

6.1.2 Tissues to be Treated or Protected

It should be recognized that any and all tissue, skin or hair can be treated or protected topically in accordance with the present invention. However, the preferred tissues to be treated or protected according to the methods of the present invention are mucosal tissues. These tissues include, but are not limited to, alveolar, esophageal, gastric, gingival, laryngeal, lingual, nasal, olfactory, oral, pharyngeal, respiratory, tracheal and vaginal mucosa, as well as mucosa of the auditory tube, bronchi, ductus deferens, urethra, gallbladder, seminal vesicle, small intestine, tympanic cavity, ureter, urinary bladder and uterine tube. More preferred are mucosal tissues of the head and neck region, which include but are not limited to, esophageal, gingival, laryngeal, lingual, nasal, olfactory, oral, pharyngeal and tracheal mucosa, as well as mucosa of the tympanic cavity.

The invention is particularly well-suited to prevent or treat damage to the mucosal tissues of the oral cavity to prevent or treat mucositis and related conditions and complications, including severe dry-mouth known as xerostomia. Thus, oral mucosal tissues are most preferred.

The term "protect" as used herein means to avoid, reduce the incidence of, or reduce the severity of mucositis and related conditions and complications and their symptoms.

The term "treat" as used herein means to lessen or reverse the symptoms of mucositis and related conditions and complications.

6.1.3 Compositions and Formulations

The aminophosphorothioate or aminoalkyl thiol compounds described herein, or pharmaceutically acceptable salts and/or hydrates thereof, may be administered singly, in combination with other compounds of the invention, and/or in combination with other therapeutic agents, including cancer chemotherapeutic agents. The active compound(s) may be administered alone or in the form of a pharmaceutical composition, wherein the active compound(s) is in admixture with one or more pharmaceutically acceptable carriers, excipients or diluents.

Suitable excipients, carriers and diluents are well known to those skilled in the pharmaceutical arts, and include those which are suitable for formulating topical preparations. When the tissues to be treated are mucosal tissues, including oral mucosa, suitable excipients, carriers and diluents must also be safe for application to oral and related mucosal tissue. These are well known to the skilled artisan.

Examples of excipients, carriers and diluents include, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. The skilled artisan can readily select the particular excipients, carriers and diluents appropriate to the type and location of the tissue to be treated.

Additionally, moisturizers or humectants can be added to the present composition if desired. Examples of such additional ingredients can be found in *Remington's Pharmaceutical Sciences,* 16th and 18th eds., Mack Publishing, Easton Pa. (1980 & 1990).

In addition to these and other vehicles which are known to those of ordinary skill in the art, it will be understood that the pharmaceutical compositions of the present invention may optionally include other ingredients such as analgesics, anesthetics, antibacterial, antiyeast agents, antifungal agents, antiviral agents, antidermatitis agents, antipruritic agents, other anti-inflammatory agents, antihyperkeratolytic agents, anti-dry skin agents, antipsoriatic agents, antiseborrheic agents, antihistamine agents, vitamins, corticosteroids, hormones, retinoids, topical cardiovascular agents, clotrimazole, ketoconazole, miconozole, griseofulvin, hydroxyzine, diphenhydramine, pratnoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate and mixtures thereof.

Depending upon the specific tissue to be treated, additional components may be used prior to, in conjunction with, or subsequent to treatment with the active component(s). For example, penetration enhancers may be used to assist in delivering the active component, e.g., amifostine, to the tissue. Suitable penetration enhancers include acetone, various alcohols (e.g. ethanol, oleyl, tetrahydrofuryl, etc.), alkyl sulfoxides such as dimethyl sulfoxide, dimethyl acetamide, dimethyl formamide, polyethylene glycol, pyrrolidones such as polyvinylpyrrolidone, Kollidon grades (Povidone, Polyvidone), urea, and various water-soluble or insoluble sugar esters such as Tween 80 (polysorbate 80) and Span 60 (sorbitan monostearate).

The pH of the composition, or of the tissue to which the compound(s) is applied, may also be adjusted to improve delivery of the compound. Preferably, the pH is somewhat basic, as a basic pH is believed to enhance the stability of the active compounds. A pH of about 8 to 9 is preferred. Similarly, the polarity of the solvent, its ionic strength or tonicity may be adjusted to improve delivery. In addition, compounds such as stearates may be added to compositions comprising the active compound(s) to advantageously alter the hydrophilicity or lipophilicity of the compound(s) and improve skin delivery. In this regard, stearates can serve as a lipid vehicle for the formulation, as an emulsifying agent or surfactant, and as a delivery-enhancing or penetration-enhancing agent. Also, different salts, hydrates or solvates of the active compounds may be used to further adjust the properties of the resulting composition.

The compounds can be formulated in compositions such as creams, lotions, ointments, gels, solutions, suspensions or other forms known to one of skill in the art and described in, for example, *Remington's Pharmaceutical Sciences,* 16th and 18th eds., Mack Publishing, Easton Pa. (1980 & 1990), and *Introduction to Pharmaceutical Dosage Forms,* 4th ed., Lea & Febiger, Philadelphia (1985). Most compositions of the present invention may be formulated as a solution, gel, lotion, cream or ointment in a pharmaceutically acceptable form. Actual methods for preparing pharmaceutical compositions are known or apparent to those skilled in the art and are described in detail in, for example, *Remington's Pharmaceutical Sciences,* 16th and 18th eds., Mack Publishing, Easton Pa. (1980 & 1990).

In a preferred embodiment for use in treating mucosal tissues within the oral cavity, the active ingredient is formulated into a solution suitable for use as a mouthwash or as an oral gel.

Several preferred example formulations suitable for application to mucosal tissues are given in the Examples below.

6.1.4 Methods and Dosages

The compounds or pharmaceutical compositions containing them are applied topically to the mucosal tissue. The term "topical" as used herein includes any route of administration that enables the compounds to line the mucosal tissue; i.e., it includes any route of administration other than parenteral or per os. Topical includes, for example, spray application, smearing, soaking and gargling.

The specific form of the compounds and their manner of administration depends in part upon the particular tissue to be treated. The compounds or pharmaceutical compositions containing them can be applied, for example, as a mouthwash to coat the oral mucosal tissue, as a spray or syringe to coat the mucosal tissues of the nose and/or throat, or as a cream or paste, an enema, or other forms of topical administration known to one of skill in the art, as appropriate.

The amount of compound to be delivered, as well as the dosing schedule necessary to provide the desired radio/chemo protective effects, will be dependent upon the bioavailability of the specific compound selected (and/or an active metabolite thereof), the disorder being treated, the radiation and/or chemotherapeutic dosage schedule, and other factors that will be apparent to those of skill in the art.

When the compound is amifostine, preferably it will be administered at a dosage of about 10 to 600 mg per dose, more preferably at 100 to 300 mg per dose, and most preferably about 200 mg per dose. It should be understood that the preferred dosages are for localized administration, and if protection for a large amount of tissue is desired, the dosage should be adjusted accordingly. The most preferred dosage of 200 mg per dose is appropriate, for example, for a typical application such as a mouthwash to protect oral mucosal tissues.

For topical application, it is convenient to provide the active compound in a pharmaceutical preparation at a concentration which will facilitate easy application of the appropriate dosage, i.e., the concentration should be chosen so that the volume of preparation to be applied is not too great or too small. For typical treatment, a convenient volume for topical application is about 1 to 30 mL per application. Thus, for example, when the desired dosage is 200 mg, it is convenient to formulate the compound in a preparation at a concentration of about 20 mg/mL, so that the desired dosage is administered by topically applying about 10 mL of the preparation. However, in particular situations it may be desirable to formulate the compound in a smaller or larger volume. One of skill in the art can readily determine a convenient concentration for a desired dosage.

While the dosage ranges given above are the preferred ranges for amifostine, these ranges should be adjusted according to the molecular weight of the active compound to deliver an equivalent number of moles. Thus, for example, a dosage of about 200 mg amifostine is equivalent to a dosage of about 130 mg WR-1065 if all other factors are equivalent.

The compounds may be administered prior to, during, or subsequent to radiation or chemotherapeutic treatment. Preferably, in order to protect against tissue damage, the compounds will be administered to the tissue up to about 90 minutes prior to each radiation or chemotherapy treatment, and more preferably up to about 30 minutes prior to each radiation or chemotherapy treatment.

The administration can be intermittent or continuous, and can continue or resume during or after treatment. Thus, for example, with specific amounts and compounds given only by way of illustration, for the treatment of oral mucosa about 10 mL of a mouthwash formulation containing about 20 mg/mL of amifostine may be administered to a patient 5 to 30 minutes before irradiation or before administration of a chemotherapeutic agent. The formulation can be rinsed and/or gargled in the mouth for about 10 seconds to about 2 minutes, then spit out. Additional dosages administered in a similar manner can be given during treatment as, for example, between different chemotherapeutic agents in a regimen incorporating multiple chemotherapeutic agents per treatment.

Alternatively, the compound may be administered in a gel, lotion, ointment or other suitable form which is applied to the tissue up to about 90 minutes before irradiation or chemotherapeutic treatment and remains on the tissue during the treatment.

The same dosage and concentrations can also be used when the compound is administered after irradiation and/or chemotherapeutic treatment. It should be understood that each of the three administrations (before, during and after radio- and/or chemotherapy treatment) may be used alone, or in any combination of two or all three administrations, as needed.

6.2. Antibacterial Properties of Amifostine and Related Compounds

The present invention also encompasses methods of preventing and treating infections, particularly those associated with mucositis, such as secondary infections that occur as a result of radiation and/or chemotherapy. Bacterial infection of mucosal tissues is a common side effect of radiation and chemical damage associated with radio/chemo cancer treatments. Damage to the mucosal basal epithelium, and resultant ulceration, leaves the exposed underlying tissues extremely susceptible to bacterial infection.

It is surprisingly discovered that amifostine and related compounds are broad spectrum antibiotics as described in the *United States Pharmacopeia,* 23rd ed. (1995), "Antimicrobial Preservatives—Effectiveness" test protocol. Thus, pharmaceutical preparations containing amifostine and related compounds can be self-preserving. This self-preserving property is particularly advantageous for use in multi-dose formulations.

The antibacterial properties can also be used advantageously to prevent and treat infections, particularly those associated with mucositis, when the amifostine compounds are applied topically. The antibacterial properties allow the topical use of the amifostine compound after irradiation or chemotherapy to protect against bacterial infection as well as symptoms of mucositis.

The types of secondary bacterial infections that can be readily treated include gram negative, gram positive, yeast, mold and pseudomonas infections.

Certain embodiments of the invention are illustrated, and not limited, by the following working examples.

7. EXAMPLES

7.1. Example 1

Effect of Topical Administration of Amifostine on Radiation-induced Mucositis in Mice The effect of topical amifostine on murine oral mucosa exposed to radiation was studied, to determine the radioprotective effects of topically and systemically applied amifostine.

Materials and Methods

The experimental model used was the inferior lip mucosa of the mice. The experimental murine model was developed by Parkins et al., *Radiother. Oncol.,* 1, 159–165 (1983), which has been shown to be a reproducible tool to study mucosal reactions after irradiation in mice. C57BL/6 mice 8–10 weeks old were used and fed with semi-liquid food.

Unanesthetized mice were maintained in supine position and irradiated exclusively on the tip of the mouth. The mice were immobilized in jigs comparable to those described in Ang et al., *Int. J. Radiat. Oncol. Biol. Phys.*, 8, 145–148 (1982). The irradiation was performed with an RT 250 Phillips apparatus, delivering 1.98 Gy/min (200 kV, 20 mA, filter of 0.2 mm Cu). During irradiation, a constant normobaric air renewal was maintained.

For the systemic applications, amifostine was dissolved in a 9% NaCl solution 5 minutes before systemic IP injection of 200 to 400 mg/kg, which was administered 30 minutes before irradiation. A placebo solution of 9% NaCl was used for a control group. For the topical applications, 50 mg of amifostine was dissolved in 1 mL of a solution containing 1% stearate, 5% $H_2O$, and ammonia to adjust the pH of the solution to 8.8. The topical application was administered to the lip mucosa of the mice for a period of 30 minutes before each radiation session, and was maintained throughout the duration of irradiation. A single dose of 16.5 Gy, and a fractionated schedule delivering 24 Gy in 4 fractions over 2 days (with 8 hour intervals between fractions) were administered.

The effect of irradiation on lip mucosa was evaluated using the scoring system described by Parker, and shown in Table 1.

TABLE 1

Parkins scoring system

| Score | Mucosal Observation/Erythema |
|---|---|
| 0.5 | doubtful if abnormally pink |
| 1 | slight but definite reddening |
| 2 | severe reddening |
| 3 | focal desquamation |
| 4 | exudation or crusting covering about ½ lip area |
| 5 | exudation or crusting covering more than ½ lip area |

Separate score for edema (swelling) of the lips, to be added to the erythema scores giving a maximum score of 7:

| Score | Mucosal Observation/Edema |
|---|---|
| 0.5 | 50-50 doubtful if any swelling |
| 1 | slight but definite swelling |
| 2 | severe swelling |

Four groups of eight mice were scored and weighed each day. Any mice having lost 30% or more of the initial weight was sacrificed. The effect of mucositis and weight loss were compared at the maximum of the acute reactions (day 11) among the different groups receiving or not receiving amifostine treatments, using the Mann and Whitney test.

Results

In a first set of experiments, the mice were irradiated with a single dose of 16.5 Gy. The distribution of weight loss and of the score of mucosal reactions after IP and topical administration is shown in FIG. 1. The maximum mucosal reactions were observed on day 11, following the start of irradiation. The mucosal reaction grades of the mice are shown in FIG. 2. The grades of mucosal reactions were significantly lower in the groups receiving amifostine compared to the control group. The Figure shows that the mucosal grades for IP administered amifostine are lower, but the difference was not found to be statistically significant.

Similar results were found in a second experiment, in which a fractionated schedule of 24 Gy in 4 fractions over 2 days was delivered using two different levels of amifostine IP: 200 mg/kg and 400 mg/kg. 400 mg/kg given before each fraction of radiation was the maximum tolerated dose. In this experiment, the topical amifostine was administered as described above without modification.

The maximum grade of mucosal reactions occurred on day 11 after irradiation, and was found to be 3.5±0.2 and 2.5±0.4 for the 200 and 400 mg/kg IP dosages, respectively. The error bars represent the standard error. For topical amifostine, the maximum grade of mucositis was found to be 3.9±0.2, and was not statistically significantly different from the IP groups. The control group receiving no amifostine showed a mucosal reaction grade of 5.6±0.4, and was statistically different (p=0.001) from the amifostine groups.

7.2. Example 2

Antibacterial Properties of Amifostine

Amifostine was studied for its ability to inhibit microbial growth. Clear 10 cc vials, stoppers and seals were sterilized for use in the study. Two separate procedures were performed: a refrigerated storage study (2° to 8° C.) and a room temperature storage study (20° to 25° C.). For each test portion, positive controls were prepared for each organism by placing 9.5 mL sterile 0.9% sodium chloride into separate sterile vials and inoculating each with $10^3$ to $10^4$ of one of the test organisms. In addition, amifostine test specimens were prepared for each test portion by reconstituting six Ethyol® vials with 0.9% sodium chloride, the contents of each of these vials were then transferred to clear sterile vials to allow for easier visual examination. One vial was designated as a negative control, and each of the remaining five vials was inoculated with $10^3$ to $10^4$ of one of the test organisms. All vials were protected from light throughout the test to simulate the amber Ethyol® vial.

Test Performance

Refrigerated Storage (2°–8° C.)

Positive controls, product test specimens, and a negative control were prepared. At this time, population counts were performed on each positive control. Population counts were also performed on positive controls and product test specimens at 24, 48 and 72 hours. These samples were diluted with sterile water and plated in duplicate with a target of 30 to 300 colonies per plate. *Candida albicans*, *Escherichia coli*, *Pseudomonas aeruginosa*, and *Staphylococcus aureus* were overpoured with TSA agar and incubated at 30–35° C. for 48 hours. *Aspergillus niger* was overpoured with Sabouraud agar and incubated at 20–25° C. for 48 hours. The plates were counted and the population counts are summarized in Table 2.

TABLE 2

Refrigerated Storage (2°–8° C.)

| | Time (hr) | CFU/mL in Amifostine | % Change | CFU/mL in Saline | % Change |
|---|---|---|---|---|---|
| S. aureus | 0 | $9.50 \times 10^{1*}$ | | $9.50 \times 10^1$ | |
| | 24 | $4.75 \times 10^1$ | −50.0% | $4.75 \times 10^1$ | −50% |
| | 48 | $4.75 \times 10^1$ | −50.0% | $4.75 \times 10^1$ | −50% |
| | 72 | $4.75 \times 10^1$ | −50.0% | $4.75 \times 10^1$ | −50% |
| P.aeruginosa | 0 | $3.80 \times 10^{3*}$ | | $3.80 \times 10^3$ | |
| | 24 | $3.04 \times 10^3$ | −20.0 | $3.47 \times 10^3$ | −0.08 |
| | 48 | $1.76 \times 10^3$ | −53.7 | $1.48 \times 10^3$ | −61.0 |
| | 72 | $1.85 \times 10^3$ | −51.3 | $2.23 \times 10^3$ | −41.3 |
| E.coli | 0 | $9.50 \times 10^{2*}$ | | $9.50 \times 10^2$ | |
| | 24 | $2.85 \times 10^2$ | −70.0 | $1.90 \times 10^2$ | −80.0 |
| | 48 | 0 | −100 | $4.75 \times 10^1$ | −95.0 |
| | 72 | 0 | −100 | 0 | −100 |

TABLE 2-continued

Refrigerated Storage (2°–8° C.)

| | Time (hr) | CFU/mL in Amifostine | % Change | CFU/mL in Saline | % Change |
|---|---|---|---|---|---|
| C.albicans | 0 | 1.08 × 10$^4$* | | 1.08 × 10$^4$ | |
| | 24 | 3.99 × 10$^3$ | −63.0 | 7.70 × 10$^3$ | −28.7 |
| | 48 | 2.09 × 10$^3$ | −80.6 | 5.52 × 10$^3$ | −48.9 |
| | 72 | 7.13 × 10$^3$ | −34.0 | 5.70 × 10$^3$ | −47.2 |
| A.niger | 0 | 3.00 × 10$^5$* | | 3.00 × 10$^5$ | |
| | 24 | 1.78 × 10$^5$ | −40.7 | 1.57 × 10$^5$ | −47.7 |
| | 48 | 1.67 × 10$^5$ | −44.3 | 1.38 × 10$^5$ | −54.0 |
| | 72 | 1.67 × 10$^5$ | −44.3 | 1.53 × 10$^5$ | −49.0 |

*theoretical

At 48 hours, the concentrations of viable microorganisms were reduced by ≧44.3% of the initial concentration. Incubation for an additional 24 hours demonstrated continued loss of viability.

Room Temperature Storage (20°–25° C.)

Positive controls, product test specimens, and a negative control were prepared. At this time, population counts were performed on each positive control. Population counts were also performed on positive controls and product test specimens at 24 and 48 hours. These samples were diluted with sterile water and plated in duplicate with a target of 30 to 300 colonies per plate. Candida albicans, Escherichia coli, Pseudomonas aeruginosa, and Staphylococcus aureus were overpoured with TSA agar and incubated at 30–35° C. for 48 hours. Aspergillus niger was overpoured with Sabouraud agar and incubated at 20–25° C. for 48 hours. The plates were counted and the population counts are summarized in Table 3.

TABLE 3

Room Temperature Storage (20°–25° C.)

| | Time (hr) | CFU/mL in Amifostine | % Change | CFU/mL in Saline | % Change |
|---|---|---|---|---|---|
| S.aureus | 0 | 1.00 × 10$^5$* | | 1.00 × 10$^5$ | |
| | 24 | 9.60 × 10$^4$ | −4.0% | 1.01 × 10$^5$ | 0% |
| | 48 | 3.32 × 10$^2$ | −99.7% | 0 | −100% |
| P.aeruginosa | 0 | 2.61 × 10$^3$* | | 2.61 × 10$^3$ | |
| | 24 | 5.22 × 10$^2$ | −80.0 | 2.09 × 10$^3$ | −21.0 |
| | 48 | 0 | −100 | 1.33 × 10$^3$ | −49.0 |
| E.coli | 0 | 2.79 × 10$^4$* | | 2.79 × 10$^4$ | |
| | 24 | 2.28 × 10$^3$ | −91.8 | 2.90 × 10$^3$ | −89.6 |
| | 48 | 8.55 × 10$^2$ | −96.9 | 9.50 × 10$^1$ | −99.6 |
| C. albicans | 0 | 1.66 × 10$^4$* | | 1.66 × 10$^4$ | |
| | 24 | 1.43 × 10$^4$ | −13.8 | 1.66 × 10$^4$ | 0 |
| | 48 | 1.00 × 10$^4$ | −39.8 | 1.44 × 10$^4$ | −13.2 |
| A. niger | 0 | 9.10 × 10$^6$* | | 9.10 × 10$^6$ | |
| | 24 | 1.56 × 10$^7$ | +58.3 | 1.73 × 10$^7$ | +52.6 |
| | 48 | 3.52 × 10$^6$ | −61.3 | 5.46 × 10$^6$ | −40.0 |

*theoretical

At 48 hours, a population count was performed on the negative control and all test samples were subcultured for microbial identification. Results revealed that the negative control was absent of microbial growth and all test specimens contained the stated test organisms.

At 24 hours, the concentration of viable bacteria were reduced in four of the five compendial organisms. The concentration of A. niger increased at 24 hours, but decreased significantly at 48 hours.

7.3. Example 3

Antibacterial Properties of WR-1065

WR-1065 was evaluated according to a protocol based on the "Antimicrobial Preservatives-Effectiveness" Test, outlined in the United States Pharmaeopeia, 23rd ed. (1995).

Procedure

Preparation of Mold Spore Inoculum Suspension

A sterile swab is used to spread 1.0 mL of a spore suspension over the surface of solidified SDA in a 150×15 mm Petri dish so as to result in a confluent lawn of mold growth. The culture is then incubated at 20–25° C. for 7 days to allow for mature spore development. Following incubation, the spores are harvested in approximately 25 mL of sterile 0.9% Saline with Polysorbate® 80 by spreading the fluid across the surface of the culture and gently scraping with a sterile spoonula to dislodge the spores. The resulting suspension is transferred into a sterile tissue grinder and the piston is reciprocated several times to break up spore chains. A spore count is obtained with the aid of a hemocytometer and the spore concentration is adjusted, if necessary, to approximately 1.0×10$^8$ spores/mL.

Preparation of the Bacterial and Yeast Inoculum Suspensions

Bacterial challenge organisms are inoculated onto TSA slants from stock cultures and incubated for 18–24 hours at 30–35° C. The yeast challenge organism is inoculated onto a SDA slant from stock culture, and incubated for 48 hours at 20–25° C. Following incubation, organisms are harvested from the agar surfaces in 0.9% Saline. Cell population in each suspension is estimated by determining percent transmittance on a spectrophotometer and consulting established growth curves for each organism. Each suspension is adjusted to an approximate concentration of 1.0×10$^8$ Colony Forming Units (CFu) per mL. The number of viable microorganisms in each inoculum suspension is determined by plate count procedure, and the initial concentration of microorganisms per gram (or mL) of WR-1065 is calculated. The numbers obtained from this procedure provide the theoretical concentration of challenge organisms present in each test article at the start of the study, and are used as the baseline for calculating the reduction of the number of organisms over time.

Neutralization

The neutralizer medium used as a diluent is AOAC Neutralizer Blanks. MCT agar is used as the plating medium for all bacteria recovery. SDA/L is used as the plating medium for fungal recovery.

A neutralization study is conducted to evaluate the preservative neutralizing ability of the media used to conduct the test and to assure that viable organisms can be detected under the conditions of the test. Separate 1:10 (and 1:100, if necessary) dilutions of WR-1065 are prepared in diluent for each test organism. A blank control of the same volume is also prepared for each organism. Each dilution and control tube is inoculated with 0.1 mL of organism suspension to result in a level of approximately 10–100 CFU/mL of suspension. Plate counts are obtained on each suspension. After incubation, colony forming units are enumerated and percent recovery between control plates and test plates is evaluated. Neutralization is effective if 50% or greater recovery is observed on test plates as compared to the inoculum control plates.

Plating and Plate Incubation

Plates prepared in this study are incubated according to the following standard:

MCT plates for bacteria recovery: 2–3 days at 30–35° C.
SDA/L plates for fungal recovery: 5–7 days at 20–25° C.
All plating for this study is conducted in duplicate.

Initial Count Procedure

Prior to inoculation of the test article, a 1:10 dilution is prepared in diluent and 1.0 mL is plated. Additional serial dilutions are prepared and plated as necessary. Two separate sets are prepared as above. One set is prepared for bacteria counts, and one set is prepared for yeast/mold counts.

Inoculation of Test Article

Five separate 20 g (or 20 mL, as appropriate) portions of the test article are placed into sterile 50 mL polypropylene conical tubes and inoculated with 0.1 mL of individual inoculum suspension to result in a final concentration of between $1.0 \times 10^5$ and $1.0 \times 10^6$ CFU/g (or mL) of test article. All inoculated specimens are vigorously mixed to assure even dispersal of the inoculum. Inoculated test articles are held at 20–25 ° C. for the duration of the study.

Post Inoculation Procedure

Enumeration of viable bacterial and fungal populations in the inoculated test article is conducted at 7, 14, 21 and 28 days post inoculation. At each time interval, a 1.0 g (or mL) specimen is removed from each inoculated specimen and plate counts are obtained by preparing serial dilutions in 9 mL tubes of diluent and plating aliquots from each dilution. Following incubation, plates are observed and the CFU's are enumerated. The number obtained is multiplied by the dilution factor to give the number of viable organisms per g (or mL) of test article at each time interval. At each time interval, the inoculated product is examined and any changes observed in the appearance of the test article during the challenge period are recorded.

WR-1065 was tested according to the procedure described above. The results are shown in Table 4.

TABLE 4

| | Test Organism Recovery (CFU/g) | | | | |
|---|---|---|---|---|---|
| Test Organism | Inoculum Counts* | 7 Day | 14 Day | 21 Day | 28 Day |
| E. coil ATCC 8739 | $4.9 \times 10^5$ | <10 | <10 | <10 | <10 |
| P. aeruginosa ATCC 9027 | $5.5 \times 10^5$ | <10 | <10 | <10 | <10 |
| S. aureus ATCC 6538 | $4.1 \times 10^5$ | $8.8 \times 10^4$ | <10 | <10 | <10 |
| C. albicans ATCC 10231 | $4.5 \times 10^5$ | $3.0 \times 10^4$ | <10 | <10 | <10 |
| A. niger ATCC 16404 | $3.5 \times 10^5$ | $1.7 \times 10^5$ | $1.3 \times 10^5$ | $1.2 \times 10^5$ | $7.5 \times 10^4$ |

*Calculated CFU/g of sample

The initial counts of bacteria, yeast and mold were <10 CFU/g.

Interpretation

The efficacy of WR-1065 was evaluated according to the following criteria stated in the *United States Pharmacopeia*, USP 23, 1995:

The preservative is effective in the product examined if: (a) the concentrations of viable bacteria are reduced to not more than 0.1% of the initial concentration by the 14th day; (b) the concentrations of viable yeast and mold remain at or below the initial concentrations during the first 14 days; and (c) the concentration of each test organism remains at or below these designated levels during the remainder of the 28 day test period.

According to these criteria, WR-1065 is an effective preservative for each of the tested microorganisms.

7.4. Example 4

Solubility of WR-1065 Salts

As mentioned above, salts of amifostine and related compounds are included within the scope of the invention. Certain salts may have advantages in topical administration. Several salts of WR-1065 were prepared, and their solubility in various solvents was measured. The data are shown in Table 5.

TABLE 5

Solubility of WR-1065 Salts

| Salt | M.W. (g/mol) | Solvent | Est. Solubitity at Saturation (mg/mL) | Est. Solubitity HPLC Assay (mg/mL) |
|---|---|---|---|---|
| Succinate | 252 | Water | 854 | 715 |
| Succinate (as free base) | | | 455 | 381 |
| Succinate | | Ethanol | insoluble | 1.95 |
| Succinate (as free base) | | | | 1.04 |
| Pamoate | 522.6 | 70% isopropyl alcohol | 21 | 18.5 |
| Pamoate (as free base) | | | 5.34 | 4.8 |
| Pamoate | | Ethanol | insoluble | 0.2 |
| Pamoate (as free base) | | | | 0.05 |
| Bis TFA* | 362.3 | Water | 820 | 954 |
| Bis TFA* (as free base) | | | 354 | 353 |
| Bis TFA* | | Ethanol | 313 | 327 |
| Bis TFA (as free base) | | | 116 | 121 |
| di-HCl | | Water | | 849 |
| di-HCl (as free base) | | | | 550 |

*Trifluoroacetate

7.5. Example 5

Formulations

Several pharmaceutical ointments were prepared for use with amifostine for topical application to oral mucosal tissue. Each of these formulations has a pH of 8.8, adjusted by addition of ammonia. The ointment bases are summarized in Table 6.

TABLE 6

Ointment Base Compositions

| Base # | Component | Amount |
|---|---|---|
| 1 | Tween 80 | 5 mL |
|  | Glycerol starch* | 100 g |
|  | Water (sterile, demineralized) | 5 mL |
|  | Ammonia | to pH 8.8 |
| 2 | Tween 80 | 5 mL |
|  | Glycerol starch | 100 g |
|  | Stearates | 1 g |
|  | Ammonia | to pH 8.8 |
| 3 | Tween 80 | 5 mL |
|  | Glycerol starch* | 100 g |
|  | Stearates | 1.5 g |
|  | Ammonia | to pH 8.8 |
| 4 | Lactose | 10 g |
|  | Water (sterile, demineralized) | 10 mL |
|  | Petrolatum | 60 g |
|  | Ammonia | to pH 8.8 |

Tween 80 is a water-soluble ester (polyoxyethylene oxide sorbitan monooleate, or polysorbate 80). Glycerol starch is a gelatinous mixture of glycerol and starch, suitable as a base for a gel or ointment. Other similar components may be used as well.

Compositions according to the present invention were prepared by first mixing amifostine in a minimal quantity (40 µL for 50 mg of amifostine) of a 9% sodium chloride solution, then combining with the ointment base. Formulations were prepared at amifostine concentrations of 20, 100 and 200 mg/mL of ointment base.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed is:

1. A method of protecting mucosal tissue in the head and/or neck region of a human in need thereof from mucositis and the symptoms thereof, which comprises topically administering to the mucosal tissue of the human a therapeutically effective amount of at least one compound having the formula

$R_1NH(CH_2)_nNH(CH_2)_mSR_2$ wherein $R_1$ is hydrogen, $C_5$–$C_7$ aryl, $C_2$–$C_7$ acyl, or $C_1$–$C_7$ alkyl; $R_2$ is hydrogen, $PO_3H_2$ or $R_3$, wherein $R_3$ is $R_1NH(CH_2)_nNH(CH_2)_mS$—; n is an integer from 1 to 10; and m is an integer from 1 to 10, or a pharmaceutically acceptable salt, solvate or hydrate thereof, wherein the mucositis is induced by treatment with radiation and/or chemotherapeutic agents.

2. The method of claim 1, wherein $R_1$ is hydrogen or methyl, $R_2$ is hydrogen or $PO_3H_2$, m is 2 or 3, and n is 3.

3. The method of claim 1, wherein the compound is amifostine, WR-1065, WR-151326, WR-151327, or WR-33278, or a pharmaceutically acceptable salt, solvate or hydrate thereof.

4. The method of claim 3, wherein the compound is amifostine, or a pharmaceutically acceptable salt, solvate or hydrate thereof.

5. The method of claim 3, wherein the compound is WR-1065, or a pharmaceutically acceptable salt, solvate or hydrate thereof.

6. The method of claim 1, wherein the compound is administered in the form of a pharmaceutical composition comprising the compound and a pharmaceutically acceptable excipient, carrier or diluent.

7. The method of claim 6, wherein the composition further comprises a penetration enhancing agent or a pH adjusting agent.

8. The method of claim 1, wherein the mucositis is induced at least in part by radiation.

9. The method of claim 8, wherein the compound is administered to the mucosal tissue of the human prior to radiation treatment, during radiation treatment, or both prior to and during radiation treatment.

10. The method of claim 9, wherein the compound is administered to the mucosal tissue no more than about 90 minutes prior to each radiation treatment.

11. The method of claim 9, wherein the compound is administered in a dosage of 10 to 600 mg.

12. The method of claim 11, wherein the compound is administered in a dosage of 100 to 300 mg.

13. The method of claim 1, wherein the mucosal tissue is esophageal mucosa, gingival mucosa, laryngeal mucosa, lingual mucosa, nasal mucosa, olfactory mucosa, oral mucosa, pharyngeal mucosa, tracheal mucosa or mucosa of the tympanic cavity.

14. The method of claim 13, wherein the mucosal tissue is oral mucosa.

15. The method of claim 1, wherein the mucositis is induced at least in part by treatment with chemotherapeutic agents.

16. The method of claim 15, wherein the compound is administered to the mucosal tissue of the human prior to treatment with chemotherapeutic agents, during treatment with chemotherapeutic agents, or both prior to and during treatment with chemotherapeutic agents.

17. The method of claim 16, wherein the compound is administered to the mucosal tissue no more than 90 minutes prior to each chemotherapy treatment.

18. The method of claim 17, wherein the compound is administered in a dosage of 10 to 600 mg.

19. The method of claim 18, wherein the compound is administered in a dosage of 100 to 300 mg.

* * * * *